United States Patent
Hesse et al.

(10) Patent No.: US 7,544,493 B2
(45) Date of Patent: Jun. 9, 2009

(54) METHOD FOR THE PURIFICATION OF AN N-TERMINAL FRAGMENT OF HEPATOCYTE GROWTH FACTOR

(75) Inventors: Friederike Hesse, Munich (DE); Martin Lanzendoerfer, Tutzing (DE); Apollon Papadimitriou, Bichl (DE); Jan Stracke, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 233 days.

(21) Appl. No.: 10/591,040

(22) PCT Filed: Mar. 2, 2005

(86) PCT No.: PCT/EP2005/002177

§ 371 (c)(1),
(2), (4) Date: Aug. 29, 2006

(87) PCT Pub. No.: WO2005/095449

PCT Pub. Date: Oct. 13, 2005

(65) Prior Publication Data

US 2007/0287827 A1    Dec. 13, 2007

(30) Foreign Application Priority Data

Mar. 3, 2004   (EP)   ................. 04004950

(51) Int. Cl.
*C12P 21/04* (2006.01)
*C12N 1/00* (2006.01)
*C12N 1/06* (2006.01)
*C12N 5/00* (2006.01)
*C12N 15/00* (2006.01)
*C07K 14/475* (2006.01)

(52) U.S. Cl. .................. 435/71.1; 435/71.2; 435/320.1; 435/325; 435/243; 435/259; 530/412

(58) Field of Classification Search ........................ None
See application file for complete search history.

(56) References Cited

U.S. PATENT DOCUMENTS

| 5,977,310 A | 11/1999 | Namiki et al. |
| 6,855,685 B2 * | 2/2005 | Nakamura ..................... 514/2 |
| 2004/0052777 A1 * | 3/2004 | Nesbit et al. ................ 424/94.1 |

FOREIGN PATENT DOCUMENTS

| EP | 1 234 583 | 8/2002 |
| WO | WO 93/23541 | 11/1993 |

OTHER PUBLICATIONS

Date et al., FEBS Letters, 420, pp. 1-6 (1997).
Albini et al., Cancer Research, 47, pp. 3239-3245 (1987).
Date et al., Oncogene, 17, pp. 3045-3054 (1998).
Kuba et al., Cancer Research, 60, pp. 6737-6743 (2000).
Miyazawa et al., Biochem. Biophys. Res. Comm., 163, pp. 967-973 (1989).
Nakamura et al., Biochem. Biophys. Res. Comm., 122, pp. 1450-1459 (1984).
Nakamura et al., Nature, 342, pp. 440-443 (1989).
Okajima et al, Eur. J. Biochem., 193, pp. 375-381 (1990).
Parr et al., Int. J. Cancer, 85, pp. 563-570 (2000).
Seki et al., Biochem. Biophys. Res. Comm., 172, pp. 321-327 (1990).
Stahl et al., Biochem. J., 326, pp. 763-772 (1997).
Stuart et al., Int. J. Exp. Path., 81, pp. 17-30 (2000).
Tashiro et al., Proc. Natl. Acad. Sci. USA, 87, pp. 3200-3204 (1990).
Weidner et al., Proc. Natl. Acad. Sci. USA, 88, pp. 7001-7005 (1991).
Brinkmann et al., Gene, 85, pp. 109-114 (1989).
Kuba et al., Biochem. Biophys. Comm., 279, pp. 846-852 (2000).
Hirao et al., Cancer Gene Therapy, 9, pp. 700-7007 (2002).

* cited by examiner

*Primary Examiner*—Marianne P Allen
(74) *Attorney, Agent, or Firm*—George W. Johnston; Patricia S. Rocha-Tramaloni; Gene J. Yao

(57) ABSTRACT

A method for the production of the N-terminal four kringle-containing fragment of hepatocyte growth factor (NK4) by expression of a nucleic acid encoding said NK4 in a microbial host cell, isolation of inclusion bodies containing said NK4 in denatured form, solubilization of the inclusion bodies and naturation of the denatured NK4, characterized in that solubilization and naturation are performed at pH 7-9 in phosphate buffered solution, provides NK4 in high purity and high yield.

8 Claims, 2 Drawing Sheets

SEQUENCE LISTING

<160> NUMBER OF SEQ ID NOS: 2

<210> SEQ ID NO 1
<211> LENGTH: 1350
<212> TYPE: DNA
<213> ORGANISM: Artificial
<220> FEATURE:
<223> OTHER INFORMATION: dna coding for NK4
<220> FEATURE:
<221> NAME/KEY: CDS
<222> LOCATION: (1)..(1350)

<400> SEQUENCE: 1

```
atg tct cgt aaa cgt cgt aat act att cat gaa ttc aaa aaa tca gca        48
Met Ser Arg Lys Arg Arg Asn Thr Ile His Glu Phe Lys Lys Ser Ala
1               5                   10                  15 aag act acc cta atc aaa ata gat cca gca ctg aag ata aaa acc aaa        96
Lys Thr Thr Leu Ile Lys Ile Asp Pro Ala Leu Lys Ile Lys Thr Lys
            20                  25                  30 aaa gtg aat act gca gac caa tgt gct aat aga tgt act agg aat aaa       144
Lys Val Asn Thr Ala Asp Gln Cys Ala Asn Arg Cys Thr Arg Asn Lys
        35                  40                  45 gga ctt cca ttc act tgc aag gct ttt gtt ttt gat aaa gca aga aaa       192
Gly Leu Pro Phe Thr Cys Lys Ala Phe Val Phe Asp Lys Ala Arg Lys
    50                  55                  60 caa tgc ctc tgg ttc ccc ttc aat agc atg tca agt gga gtg aaa aaa       240
Gln Cys Leu Trp Phe Pro Phe Asn Ser Met Ser Ser Gly Val Lys Lys
65                  70                  75                  80 gaa ttt ggc cat gaa ttt gac ctc tat gaa aac aaa gac tac att aga       288
Glu Phe Gly His Glu Phe Asp Leu Tyr Glu Asn Lys Asp Tyr Ile Arg
                85                  90                  95 aac tgc atc att ggt aaa gga cgc agc tac aag gga aca gta tct atc       336
Asn Cys Ile Ile Gly Lys Gly Arg Ser Tyr Lys Gly Thr Val Ser Ile
            100                 105                 110 act aag agt ggc atc aaa tgt cag ccc tgg agt tcc atg ata cca cac       384
Thr Lys Ser Gly Ile Lys Cys Gln Pro Trp Ser Ser Met Ile Pro His
        115                 120                 125 gaa cac agc ttt ttg cct tcg agc tat cgg ggt aaa gac cta cag gaa       432
Glu His Ser Phe Leu Pro Ser Ser Tyr Arg Gly Lys Asp Leu Gln Glu
    130                 135                 140 aac tac tgt cga aat cct cga ggg gaa gaa ggg gga ccc tgg tgt ttc       480
Asn Tyr Cys Arg Asn Pro Arg Gly Glu Glu Gly Gly Pro Trp Cys Phe
145                 150                 155                 160 aca agc aat cca gag gta cgc tac gaa gtc tgt gac att cct cag tgt       528
Thr Ser Asn Pro Glu Val Arg Tyr Glu Val Cys Asp Ile Pro Gln Cys
                165                 170                 175 tca gaa gtt gaa tgc atg acc tgc aat ggg gag agt tat cga ggt ctc       576
Ser Glu Val Glu Cys Met Thr Cys Asn Gly Glu Ser Tyr Arg Gly Leu
            180                 185                 190 atg gat cat aca gaa tca ggc aag att tgt cag cgc tgg gat cat cag       624
Met Asp His Thr Glu Ser Gly Lys Ile Cys Gln Arg Trp Asp His Gln
        195                 200                 205 aca cca cac cgg cac aaa ttc ttg cct gaa aga tat ccc gac aag ggc       672
Thr Pro His Arg His Lys Phe Leu Pro Glu Arg Tyr Pro Asp Lys Gly
    210                 215                 220 ttt gat gat aat tat tgc cgc aat ccc gat ggc cag ccg agg cca tgg       720
Phe Asp Asp Asn Tyr Cys Arg Asn Pro Asp Gly Gln Pro Arg Pro Trp
225                 230                 235                 240 tgc tat act ctt gac cct cac acc cgc tgg gag tac tgt gca att aaa       768
Cys Tyr Thr Leu Asp Pro His Thr Arg Trp Glu Tyr Cys Ala Ile Lys
```

-continued

|   |   |   |   |   |   |   |   |   |   |   |   |   |   |   |   |  |
|---|---|---|---|---|---|---|---|---|---|---|---|---|---|---|---|---|
|   |   |   | 245 |   |   |   | 250 |   |   |   | 255 |   |   |   |   |  |
| aca | tgc | gct | gac | aat | act | atg | aat | gac | act | gat | gtt | cct | ttg | gaa | aca | 816 |
| Thr | Cys | Ala | Asp | Asn | Thr | Met | Asn | Asp | Thr | Asp | Val | Pro | Leu | Glu | Thr |  |
|   |   |   | 260 |   |   |   | 265 |   |   |   | 270 |   |   |   |   |  |
| act | gaa | tgc | atc | caa | ggt | caa | gga | gaa | ggc | tac | agg | ggc | act | gtc | aat | 864 |
| Thr | Glu | Cys | Ile | Gln | Gly | Gln | Gly | Glu | Gly | Tyr | Arg | Gly | Thr | Val | Asn |  |
|   |   |   | 275 |   |   |   | 280 |   |   |   | 285 |   |   |   |   |  |
| acc | att | tgg | aat | gga | att | cca | tgt | cag | cgt | tgg | gat | tct | cag | tat | cct | 912 |
| Thr | Ile | Trp | Asn | Gly | Ile | Pro | Cys | Gln | Arg | Trp | Asp | Ser | Gln | Tyr | Pro |  |
|   |   |   | 290 |   |   |   | 295 |   |   |   | 300 |   |   |   |   |  |
| cac | gag | cat | gac | atg | act | cct | gaa | aat | ttc | aag | tgc | aag | gac | cta | cga | 960 |
| His | Glu | His | Asp | Met | Thr | Pro | Glu | Asn | Phe | Lys | Cys | Lys | Asp | Leu | Arg |  |
| 305 |   |   |   |   | 310 |   |   |   |   | 315 |   |   |   |   | 320 |  |
| gaa | aat | tac | tgc | cga | aat | cca | gat | ggg | tct | gaa | tca | ccc | tgg | tgt | ttt | 1008 |
| Glu | Asn | Tyr | Cys | Arg | Asn | Pro | Asp | Gly | Ser | Glu | Ser | Pro | Trp | Cys | Phe |  |
|   |   |   | 325 |   |   |   | 330 |   |   |   | 335 |   |   |   |   |  |
| acc | act | gat | cca | aac | atc | cga | gtt | ggc | tac | tgc | tcc | caa | att | cca | aac | 1056 |
| Thr | Thr | Asp | Pro | Asn | Ile | Arg | Val | Gly | Tyr | Cys | Ser | Gln | Ile | Pro | Asn |  |
|   |   |   | 340 |   |   |   | 345 |   |   |   | 350 |   |   |   |   |  |
| tgt | gat | atg | tca | cat | gga | caa | gat | tgt | tat | cgt | ggg | aat | ggc | aaa | aat | 1104 |
| Cys | Asp | Met | Ser | His | Gly | Gln | Asp | Cys | Tyr | Arg | Gly | Asn | Gly | Lys | Asn |  |
|   |   |   | 355 |   |   |   | 360 |   |   |   | 365 |   |   |   |   |  |
| tat | atg | ggc | aac | tta | tcc | caa | aca | aga | tct | gga | cta | aca | tgt | tca | atg | 1152 |
| Tyr | Met | Gly | Asn | Leu | Ser | Gln | Thr | Arg | Ser | Gly | Leu | Thr | Cys | Ser | Met |  |
|   |   |   | 370 |   |   |   | 375 |   |   |   | 380 |   |   |   |   |  |
| tgg | gac | aag | aac | atg | gaa | gac | tta | cat | cgt | cat | atc | ttc | tgg | gaa | cca | 1200 |
| Trp | Asp | Lys | Asn | Met | Glu | Asp | Leu | His | Arg | His | Ile | Phe | Trp | Glu | Pro |  |
| 385 |   |   |   |   | 390 |   |   |   |   | 395 |   |   |   |   | 400 |  |
| gat | gca | agt | aag | ctg | aat | gag | aat | tac | tgc | cga | aat | cca | gat | gat | gat | 1248 |
| Asp | Ala | Ser | Lys | Leu | Asn | Glu | Asn | Tyr | Cys | Arg | Asn | Pro | Asp | Asp | Asp |  |
|   |   |   | 405 |   |   |   | 410 |   |   |   | 415 |   |   |   |   |  |
| gct | cat | gga | ccc | tgg | tgc | tac | acg | gga | aat | cca | ctc | att | cct | tgg | gat | 1296 |
| Ala | His | Gly | Pro | Trp | Cys | Tyr | Thr | Gly | Asn | Pro | Leu | Ile | Pro | Trp | Asp |  |
|   |   |   | 420 |   |   |   | 425 |   |   |   | 430 |   |   |   |   |  |
| tat | tgc | cct | att | tct | cgt | tgt | gaa | ggt | gat | acc | aca | cct | aca | atc | gtt | 1344 |
| Tyr | Cys | Pro | Ile | Ser | Arg | Cys | Glu | Gly | Asp | Thr | Thr | Pro | Thr | Ile | Val |  |
|   |   |   | 435 |   |   |   | 440 |   |   |   | 445 |   |   |   |   |  |
| taa | tag |   |   |   |   |   |   |   |   |   |   |   |   |   |   | 1350 |

<210> SEQ ID NO 2
<211> LENGTH: 448
<212> TYPE: PRT
<213> ORGANISM: Artificial
<220> FEATURE:
<223> OTHER INFORMATION: protein-sequence of NK4

<400> SEQUENCE: 2

Met Ser Arg Lys Arg Asn Thr Ile His Glu Phe Lys Lys Ser Ala
1               5                   10                  15

Lys Thr Thr Leu Ile Lys Ile Asp Pro Ala Leu Lys Ile Lys Thr Lys
                20                  25                  30

Lys Val Asn Thr Ala Asp Gln Cys Ala Asn Arg Cys Thr Arg Asn Lys
            35                  40                  45

Gly Leu Pro Phe Thr Cys Lys Ala Phe Val Phe Asp Lys Ala Arg Lys
        50                  55                  60

Gln Cys Leu Trp Phe Pro Phe Asn Ser Met Ser Ser Gly Val Lys Lys
65                  70                  75                  80

Glu Phe Gly His Glu Phe Asp Leu Tyr Glu Asn Lys Asp Tyr Ile Arg
                85                  90                  95

-continued

```
Asn Cys Ile Ile Gly Lys Gly Arg Ser Tyr Lys Gly Thr Val Ser Ile
            100                 105                 110
Thr Lys Ser Gly Ile Lys Cys Gln Pro Trp Ser Ser Met Ile Pro His
        115                 120                 125
Glu His Ser Phe Leu Pro Ser Ser Tyr Arg Gly Lys Asp Leu Gln Glu
    130                 135                 140
Asn Tyr Cys Arg Asn Pro Arg Gly Glu Glu Gly Pro Trp Cys Phe
145                 150                 155                 160
Thr Ser Asn Pro Glu Val Arg Tyr Glu Val Cys Asp Ile Pro Gln Cys
                165                 170                 175
Ser Glu Val Glu Cys Met Thr Cys Asn Gly Glu Ser Tyr Arg Gly Leu
            180                 185                 190
Met Asp His Thr Glu Ser Gly Lys Ile Cys Gln Arg Trp Asp His Gln
            195                 200                 205
Thr Pro His Arg His Lys Phe Leu Pro Glu Arg Tyr Pro Asp Lys Gly
        210                 215                 220
Phe Asp Asp Asn Tyr Cys Arg Asn Pro Asp Gly Gln Pro Arg Pro Trp
225                 230                 235                 240
Cys Tyr Thr Leu Asp Pro His Thr Arg Trp Glu Tyr Cys Ala Ile Lys
                245                 250                 255
Thr Cys Ala Asp Asn Thr Met Asn Asp Thr Asp Val Pro Leu Glu Thr
            260                 265                 270
Thr Glu Cys Ile Gln Gly Gln Gly Glu Gly Tyr Arg Gly Thr Val Asn
            275                 280                 285
Thr Ile Trp Asn Gly Ile Pro Cys Gln Arg Trp Asp Ser Gln Tyr Pro
        290                 295                 300
His Glu His Asp Met Thr Pro Glu Asn Phe Lys Cys Lys Asp Leu Arg
305                 310                 315                 320
Glu Asn Tyr Cys Arg Asn Pro Asp Gly Ser Glu Ser Pro Trp Cys Phe
                325                 330                 335
Thr Thr Asp Pro Asn Ile Arg Val Gly Tyr Cys Ser Gln Ile Pro Asn
            340                 345                 350
Cys Asp Met Ser His Gly Gln Asp Cys Tyr Arg Gly Asn Gly Lys Asn
            355                 360                 365
Tyr Met Gly Asn Leu Ser Gln Thr Arg Ser Gly Leu Thr Cys Ser Met
        370                 375                 380
Trp Asp Lys Asn Met Glu Asp Leu His Arg His Ile Phe Trp Glu Pro
385                 390                 395                 400
Asp Ala Ser Lys Leu Asn Glu Asn Tyr Cys Arg Asn Pro Asp Asp Asp
                405                 410                 415
Ala His Gly Pro Trp Cys Tyr Thr Gly Asn Pro Leu Ile Pro Trp Asp
            420                 425                 430
Tyr Cys Pro Ile Ser Arg Cys Glu Gly Asp Thr Thr Pro Thr Ile Val
        435                 440                 445
```

METHOD FOR THE PURIFICATION OF AN N-TERMINAL FRAGMENT OF HEPATOCYTE GROWTH FACTOR

This application is the National Stage of International Application No. PCT/EP2005/002177, filed Mar. 2, 2005, which claims the benefit of European Application No. 04004950.4, filed Mar. 3, 2004, which is hereby incorporated by reference in its entirety.

The invention relates to a method for the purification of the N-terminal four kringle-containing fragment of hepatocyte growth factor (NK4).

BACKGROUND OF THE INVENTION

Hepatocyte growth factor (HGF/SF) is a polypeptide identified and purified by Nakamura, T., et al., Biochem. Biophys. Res. Commun. 22 (1984) 1450-1459. It was further found that hepatocyte growth factor is identical to scatter factor (SF), Weidner, K. M., et al., Proc. Natl. Acad. Sci. USA 88 (1991) 7001-7005. HGF is a glycoprotein involved in the development of a number of cellular phenotypes including proliferation, mitogenesis, formation of branching tubules and, in the case of tumor cells, invasion and metastasis. For a status review, see Stuart, K. A., et al., Int. J. Exp. Pathol. 81 (2000) 17-30.

Both rat HGF and human HGF have been sequenced and cloned (Miyazawa, K. et al., Biochem. Biophys. Res. Comm. 163 (1989) 967-973; Nakamura, T., et al., Nature 342 (1989) 440-443; Seki, T., et al., Biochem. and Biophys. Res. Comm. 172 (1990) 321-327; Tashiro, K., et al., Proc. Natl. Acad. Sci. USA 87 (1990) 3200-3204; Okajima, A., et al., Eur. J. Biochem. 193 (1990) 375-381).

It was further found that an HGF/SF fragment, termed NK4, consisting of the N-terminal hairpin domain and the four kringle domains of HGF/SF has pharmacological properties that are completely different from those of HGF/SF, and is an antagonist to the influence of HGF/SF on the motility and the invasion of colon cancer cells, and is, in addition, an angiogenesis inhibitor that suppresses tumor growth and metastasis (Parr, C., et al., Int. J. Cancer 85 (2000) 563-570; Kuba, K., et al., Cancer Res. 60 (2000) 6737-6743; Date, K., et al., FEBS Lett. 420 (1997) 1-6; Date, K., et al., Oncogene 17 (1989) 3045-3054).

NK4 is prepared according to the state of the art (Date, K., et al., FEBS Lett. 420 (1997) 1-6) by recombinant expression of HGF cDNA in CHO cells and subsequent digestion with pancreatic elastase. Two other isoforms of HGF (NK1 and NK2) encoding the N-terminal domain and kringle 1, and the N-terminal domain and kringles 1 and 2, respectively, were produced in E. coli via the inclusion body route (Stahl, S. J., Biochem. J. 326 (1997) 763-772). According to Stahl, naturation of NK1 or NK2 was performed in 100 mM TRIS/HCl pH 7.5 containing 2.5 M urea, 5 mM reduced glutathione (GSH) and 1 mM oxidized glutathione (GSSG). Purification was performed subsequently on a Superdex™ 75 column using also TRIS buffer. The use of TRIS buffer according to the state of the art during solubilization and naturation leads according to the investigations of the inventors to a considerable amount (of about 50%) of by-products which are identified by the inventors as consisting mainly of GSH-modified NK4.

Therefore this method is not useful for the recombinant production of NK4 in considerable amounts and sufficient purity (for therapeutic use).

SUMMARY OF THE INVENTION

The invention provides a method for the production of NK4 by expression of a nucleic acid encoding said NK4 in a microbial host cell, isolation of inclusion bodies containing said NK4 in denatured form, solubilization of the inclusion bodies and naturation of the denatured NK4 in the presence of GSH and GSSG, characterized in that solubilization and naturation are performed at pH 7-9 in phosphate buffered solution.

It was surprisingly found that the use of potassium phosphate buffer in a pH range between 7 and 9, preferably between pH 8 and 9, leads to a considerable improvement in yield and purity of NK4.

Preferably NK4 is dialyzed after naturation with phosphate buffer pH 7-9 for at least 24 hours. Purificaton is performed preferably by hydrophobic interaction chromatography in the presence of phosphate buffer pH 7-9, whereby the use of butyl- or phenyl sepharose as chromatographic material is especially preferred.

DETAILED DESCRIPTION OF THE INVENTION

Human HGF is a disulfide-linked heterodimer, which can be cleaved in an α-subunit of 463 amino acids and a β-subunit of 234 amino acids, by cleavage between amino acids R494 and V495. The N-terminus of the α-chain is preceded by 31 amino acids started with a methionine group. This segment includes a signal sequence of 31 amino acids. The α-chain starts at amino acid 32 and contains four kringle domains. The so-called "hairpin domain" consists of amino acids 70-96. The kringle 1 domain consists of amino acids 128-206. The kringle 2 domain consists of amino acids 211-288, the kringle 3 domain consists of amino acids 305-383, and the kringle 4 domain consists of amino acids 391-469 of the α-chain, approximately.

NK4 according to the invention consist preferably of amino acid (aa) 32-494 or an N-terminal fragment thereof (always beginning with aa 32), the smallest fragment being aa 32-478. The length of NK4 can vary within this range as long as its biological properties are not affected. In addition there exist variations of these sequences, essentially not affecting the biological properties of NK4 (especially not affecting its activities antagonistic to HGF and its antiangiogenic activities), which variations are described, for example, in WO 93/23541. The activity of NK4 is measured by a scatter assay according to example 4.

NK4 can be produced recombinantly, either by the production of recombinant human HGF/SF and digestion with elastase (Date, K., FEBS Lett. 420 (1997) 1-6) or by recombinant expression of an NK4 encoding nucleic acid in appropriate host cells, as described below. NK4 glycoprotein has a molecular weight of about 57 kDa (52 kDa for the polypeptide part alone) and has the in vivo biological activity of causing inhibition of tumor growth, angiogenesis and/or metastasis.

The NK4 polypeptides can be produced by recombinant means in prokaryotes. For expression in prokaryotic host cells, the nucleic acid is integrated into a suitable expression vector, according to methods familiar to a person skilled in the art. Such an expression vector preferably contains a regulatable/inducible promoter. The recombinant vector is then introduced for the expression into a suitable host cell such as, e.g., *E. coli* and the transformed cell is cultured under conditions which allow expression of the heterologous gene. After fermentation inclusion bodies containing denatured NK4 are isolated.

*Escherichia*, *Salmonella*, *Streptomyces* or *Bacillus* are for example suitable as prokaryotic host organisms. For the production of NK4 polypeptides prokaryotes are transformed in the usual manner with the vector, which contains the DNA coding for NK4 and subsequently fermented in the usual manner. However expression yield in *E. coli* using the original NK4 DNA sequence (GenBank M73239) is very low. Surprisingly it was found that modification of at least one of the codons of the DNA sequence encoding amino acid positions 33 to 36 (codon 33 encodes arginine, numbering according to M73239) results in an increase of expression yield of 20% polypeptide or more. Therefore, a further object of the invention is a method for the recombinant production of NK4 in prokaryotes by expression of a replicable expression vector containing DNA encoding NK4 characterized in that in said DNA at least one of the codons of amino acids selected from the group consisting of codons at positions 33, 34, 35 and 36 is modified from AGG to CGT (position 33), AAA to AAA (position 34), AGA to CGT (position 35), and/or AGA to CGT (position 36). It is further preferred that the codon for amino acid 32 is changed from encoding Gln to encoding Ser in order to improve splitting off N-terminal arginine.

Inclusion bodies are found in the cytoplasm as the gene to be expressed does not contain a signal sequence. These inclusion bodies are separated from other cell components, for example by centrifugation after cell lysis.

The inclusion bodies were solubilized by adding a denaturing agent like 6 M guanidinium hydrochloride or 8 M urea at pH 7-9 in phosphate buffer (preferably in a concentration of 0.1-1.0 M, e.g. 0.4 M) preferably in the presence of DTT (dithio-1,4-threitol). The solubilisate is diluted in phosphate buffer pH 7-9 in the presence of GSH/GSSG (preferably 2-20 mM glutathion) and a denaturing agent in a non denaturing concentration (e.g. 2M guanidinium hydrochloride or 4 M urea) or preferably instead of guanidinium hydrochloride or urea, arginine in a concentration of about 0.3 to 1.0 M, preferably in a concentration of about 0.7 M. Renaturation is performed preferably at a temperature of about 4° C. and for about 48 to 160 hours.

After naturation is terminated the solution was dialyzed preferably against phosphate buffer pH 7-9 (preferably in a concentration of 0.1-1.0 M, e.g. 0.3 M) for at least 24 hours, preferably for 24-120 hours.

NK4 polypeptide or fragments thereof can be purified after recombinant production and naturation of the water insoluble denatured polypeptide (inclusion bodies) according to the method of the invention preferably by chromatographic methods, e.g. by affinity chromatography, hydrophobic interaction chromatography, immunoprecipitation, gel filtration, ion exchange chromatography, chromatofocussing, isoelectric focussing, selective precipitation, electrophoresis, or the like. It is preferred to purify NK4 polypeptides by hydrophobic interaction chromatography, preferably at pH 7-9, in the presence of phosphate buffer and/or preferably by the use of butyl- or phenyl sepharose.

According to the method of the invention, only a minor amount of the NK4 polypeptides is modified by the formation of GSH adducts. Of the total amount of NK4 polypeptides, i.e. the amount of the inclusion bodies separated from other cell components (corresponding to 100%), the amount of GSH-modified NK4 is between 0% and 50%, preferably between 0% and 35%, and more preferably between 0% and 20%.

The following examples, references, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCES

Figure 1:
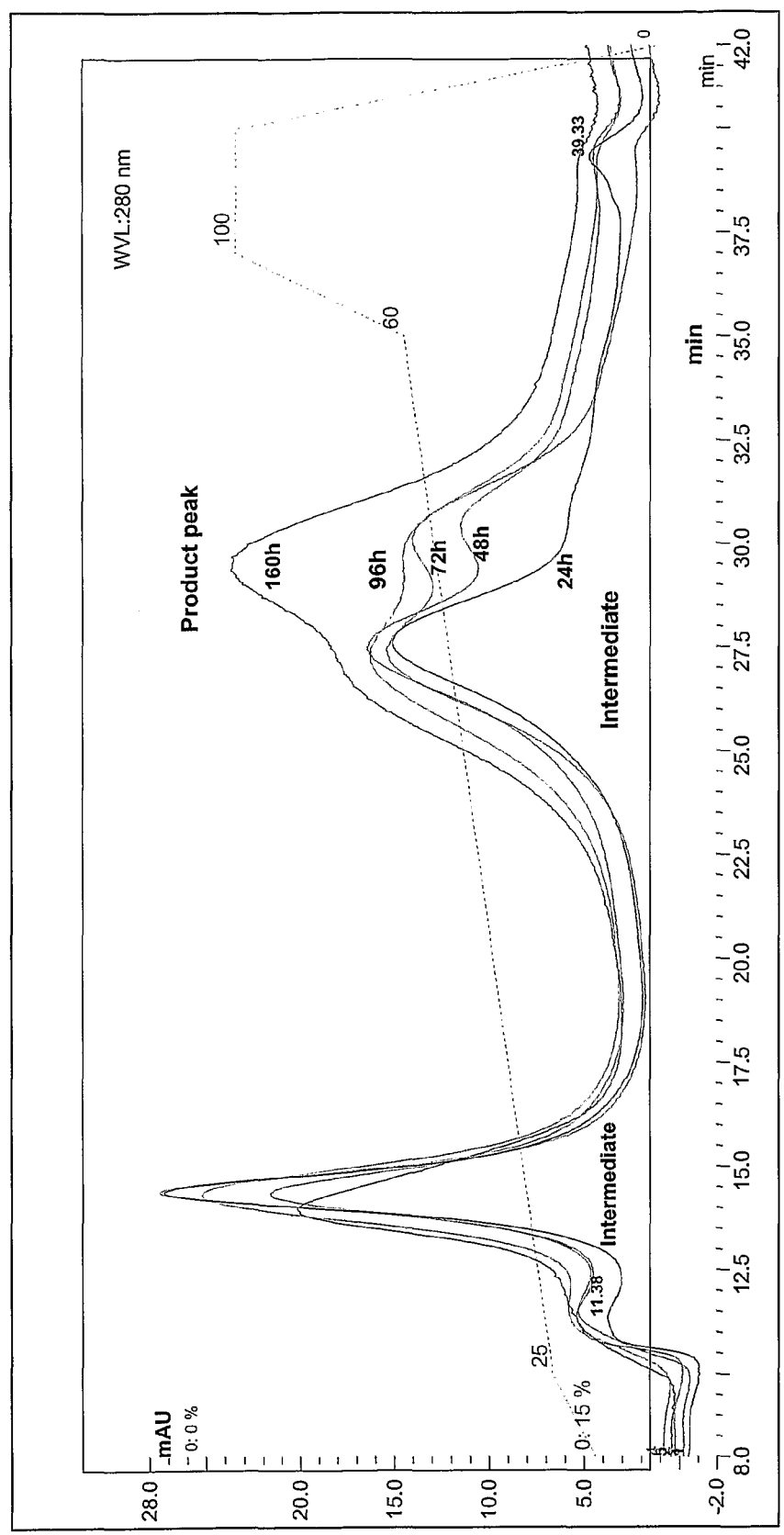
FIG. 1 Renaturation kinetics, heparin column, detection at 280 nm

SEQ ID NO:1 DNA coding for NK4
SEQ ID NO:2 Polypetide sequence of NK4

EXAMPLE 1

Recombinant Expression of NK4

The NK4 domain from amino acid position 32 to 478 of HGF was used for cloning and recombinant expression in *Escherichia coli*. The original DNA sequence used as source of DNA was described (database identifier "gb:M73239"). PCR was performed in order to amplify and concurrently modify the DNA coding for NK4 (Seq ID No:1). All methods were performed under standard conditions.

In comparison to the original DNA sequence of NK4, the following modifications were introduced:

Elimination of the eukaryotic signal peptide sequence and fusion of the ATG start codon next to amino acid position 32 of NK4 exchange of amino acid position 32 from Gln to Ser in order to improve homogeneity of the protein product (Met-free)

modification of the DNA sequence of the codons of amino acids at position 33 (AGG to CGT), 35 (AGA to CGT), and 36 (AGA to CGT) in order to improve gene expression in *E. coli*.

modification of the DNA sequence of codons at position 477 (ATA to ATC) and 478 (GTC to GTT) in order to facilitate insertion of PCR product into the vector introduction of two translational stop codons at positions 479 (TAA) and 480 (TGA), in order to stop the translation at a position equivalent to the end of NK4 protein domain.

The PCR-amplified DNA fragment was treated with restriction endonucleases NdeI and BanII and was ligated to the modified pQE vector (Qiagen) (elimination of His-tag as well as DHFR coding region), which was appropriately treated with NdeI and BanII. The elements of expression plasmid pQE-NK4-Ser (Plasmid size 4447 bp) are T5 promotor/lac operator element, NK4 coding region, lambda to transcriptional termination region, rrnB T1 transcriptional termination region, ColE1 origin of replication and β-lactamase coding sequence.

The ligation reaction was used to transform *E. coli* competent cells, e.g. *E. coli* strain C600 harbouring expression helper plasmid pUBS520 (Brinkmann, U., et al., Gene 85 (1989) 109-114). *E. coli* colonies were isolated and were characterized with respect to restriction and sequence analysis of their plasmids. The selection of clones was carried out by analysis of the NK4 protein content after cultivation of recombinant cells in LB medium in the presence of appropriate antibiotics and after induction of the gene expression by addition of IPTG (1 mM). The protein pattern of cell lysates were compared by PAGE. The recombinant *E. coli* clone showing the highest proportion of NK4 protein was selected for the production process. Fermentation was performed under standard conditions and inclusion bodies were isolated.

EXAMPLE 2

Solubilization and Naturation Using the Optimized Conditions

Inclusion bodies were dissolved over night in a buffer containing 6 M guanidinium hydrochloride, 0.1 M potassium phosphate pH 8.5 (by titration with 10 M KOH), 1 mM EDTA, 0.01 mM DTT. The concentration of the dissolved protein was determined by Biuret assay and finally adjusted to a concentration of 25 mg total protein/ml at room temperature.

This NK4-solubilisate was diluted to a concentration of 0.4 mg/ml in a buffer containing 0.7 M arginine, 0.1 M potassium phosphate pH 8.5 (by titration with conc. HCl), 10 mM GSH, 5 mM GSSG and 1 mM EDTA. This renaturation assay was incubated between 2 and 8 days at 4° C. The renaturation efficacy was measured by analytical affinity chromatgraphy using an 1 ml Heparin Sepharose column (renaturation kinetics see FIG. 1).

Buffer conditions:

| Buffer A: | 50 mM Tris pH 8.0 | |
|---|---|---|
| Buffer B: | 50 mM Tris pH 8.0, 2 M NaCl | |
| Gradient: | 5-25% | buffer B, 2 column volumes |
| | 25-60% | buffer B, 16 column volumes |
| | 60-100% | buffer B, 0.7 column volumes |
| | 100% | buffer B, 2 column volumes |

After obtaining the maximal renaturation efficacy, the renaturation assay of 15 l volume was concentrated to 3 l using a tangential flow filtration unit (MW cut off: 10 kDa, Sartorius). It was subsequently dialyzed against 3 times 50 l buffer containing 0.3 M potassium phosphate at pH 8.0 for at least 3×24 hours, optimally for 5 days in total.

Purification was performed by heparin-sepharose chromatography (conditions see above). To the eluted material 1 M ammonium sulfate in 0.1 M potassium phosphate pH 8.0 was added and incubated at 4° C. overnight. The sample was centrifuged and the supernatant was loaded on a phenyl sepharose column (150 ml). The column was washed with 1 column volume 1 M ammonium sulfate in 50 mM potassium phosphate pH 8.0.

Elution conditions:

Buffer A: 1 M ammonium sulfate, 50 mM potassium phosphate pH 8.0

Buffer B: 50 mM potassium phosphate pH 8.0, 40% ethylene glycol 0-100% buffer B, 20 column volumes

EXAMPLE 3

Comparison of Naturation Using Potassium Phosphate and Tris

Figure 2:
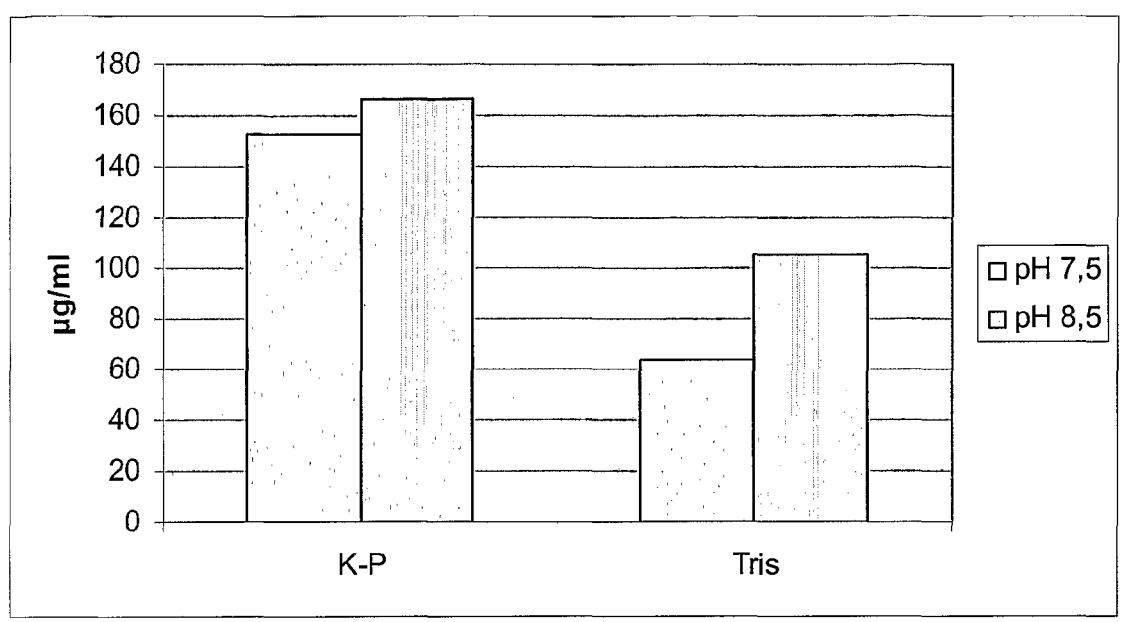
FIG. 2 Renaturation efficacies

Renaturation conditions were analyzed using potassium phosphate or TRIS at pH 7.5 and pH 8.5 (both titrated with conc. HCl) as buffering reagents. The solubilization and renaturation conditions were as described in example 2, but with 0.1 M TRIS or 0.1 M potassium phosphate in the renaturation buffer. The dialysis was also performed as described in example 2, but in 0.1 M TRIS or 0.1 M potassium phosphate. Potassium phosphate buffer (K-P) led to significantly higher renaturation yields as TRIS buffer, measured as amount of active NK4 by scatter assay (see FIG. 2).

EXAMPLE 4

Determination of Activity a) Scatter Assay

MDCK cells were subconfluently grown in tissue culture plates. Cells were treated with HGF (10 ng/ml) or with combinations of HGF and NK4. In these experiments the HGF-induced cell scattering was inhibited by the addition of a 10 to 1000-fold molar excess of NK4 at least for 90% and more, showing the functional activity.

b) Proliferation Assay

Inhibition of the mitogenic activity of HGF by NK4 was determined by measuring DNA synthesis of adult rat hepatocytes in primary culture as described in Nakamura, T., et al., Nature 342 (1989) 440-443. In these experiments the HGF-induced cell proliferation was inhibited by the addition of a 10 to 1000-fold molar excess of NK4 at least for 90% and more, showing the functional activity.

c) Invasion Assay

In this assay the invasive potential of tumor cells is analyzed. The assay was done essentially as described in Albini, A., et al., Cancer Res. 47 (1987) 3239-3245, using HT115 cells. Again, HGF-induced (10 ng/ml) cell invasion could be inhibited by a 10 to 1000-fold molar excess of NK4 at least for 90% and more, showing the functional activity.

EXAMPLE 5

Activity in Vivo

Model: Lewis Lung Carcinoma nude mouse tumor model
  $1\times10^6$ lewis lung carcinoma cells were s.c. implanted into male nude mice (BALB/c nu/nu).
Treatment: After 4 days, one application daily of pegylated NK4 over a period of 2-4 weeks
Dose: 1000 µg/mouse/day
  300 µg/mouse/day
  100 µg/mouse/day
  placebo
Result: Treatment with NK4 shows a dose dependent suppression of primary tumor growth and metastasis, whereas no effect is seen in placebo treated groups.

LIST OF REFERENCES

Albini, A., et al., Cancer Res. 47 (1987) 3239-3245
Brinkmann, U., et al., Gene 85 (1989) 109-114
Date, K., et al., FEBS Lett. 420 (1997) 1-6
Date, K., et al., Oncogene 17 (1989) 3045-3054
Kuba, K., et al., Cancer Res. 60 (2000) 6737-6743
Miyazawa, K. et al., Biochem. Biophys. Res. Comm. 163 (1989) 967-973
Nakamura, T., et al., Biochem. Biophys. Res. Commun. 22 (1984) 1450-1459
Nakamura, T., et al., Nature 342 (1989) 440-443
Okajima, A., et al., Eur. J. Biochem. 193 (1990) 375-381
Parr, C., et al., Int. J. Cancer 85 (2000) 563-570
Seki, T., et al., Biochem. and Biophys. Res. Comm. 172 (1990) 321-327
Stahl, S. J., Biochem. J. 326 (1997) 763-772
Stuart, K. A., et al., Int. J. Exp. Pathol. 81 (2000) 17-30
Tashiro, K., et al., Proc. Natl. Acad. Sci. USA 87 (1990) 3200-3204
U.S. Pat. No. 5,977,310
Weidner, K. M., et al., Proc. Natl. Acad. Sci. USA 88 (1991) 7001-7005
WO 93/23541

The invention claimed is:

1. A method for the production of a polypeptide having the amino acid sequence of SEQ ID NO: 2, comprising:
    (a) expressing a nucleic acid encoding said polypeptide in a microbial host cell,
    (b) isolating inclusion bodies containing said polypeptide in denatured form,
    (c) solubilizing the inclusion bodies at a pH of 7-9 in a phosphate buffered solution comprising a denaturing agent, and
    (d) renaturing the denatured polypeptide at a pH of 7-9 in a phosphate buffered solution comprising reduced glutathione (GSH) and oxidized glutathione (GSSG) and a denaturing agent in a non-denaturing concentration.

2. A method according to claim 1, wherein, after renaturating, the polypeptide is dialyzed with phosphate buffer at pH 7-9 for at least 24 hours.

3. A method according to claim 1, wherein the polypeptide is purified after renaturation by hydrophobic interaction chromatography in the presence of a phosphate buffer at pH 7-9.

4. A method according to claim 3, wherein the chromatography is performed on butyl sepharose or phenyl sepharose.

5. A method according to claim 1, wherein the amount of said polypeptide that is GSH-modified is between 0% and 50% of the total amount of said polypeptide.

6. A method according to claim 5, wherein the amount of said polypeptide that is GSH-modified is between 0% and 20% of the total amount of said polypeptide.

7. A method according to claim 1, wherein steps (c) and (d) are each performed at a pH between 8 and 9 and said phosphate buffered solution used in steps (c) and (d) is potassium phosphate buffer.

8. A method according to claim 1, wherein said denaturing agent used in step (c) is guanidinium hydrochloride and said denaturing agent used in step (d) is arginine.

* * * * *